United States Patent [19]

Larock

[11] 4,065,479
[45] Dec. 27, 1977

[54] METHOD OF SYNTHESIS OF PI-ALLYL-PALLADIUM COMPOUNDS

[75] Inventor: Richard Craig Larock, Ames, Iowa

[73] Assignee: Iowa State University Research Foundation, Inc., Ames, Iowa

[21] Appl. No.: 681,784

[22] Filed: Apr. 30, 1976

[51] Int. Cl.² ............................................. C07F 15/00
[52] U.S. Cl. ................................................ 260/429 L
[58] Field of Search .......................... 260/429 L, 429 R

[56] References Cited

U.S. PATENT DOCUMENTS

| 3,369,035 | 2/1968 | Schultz | 260/429 R |
| 3,398,168 | 8/1968 | Medema | 260/429 R |
| 3,446,825 | 5/1969 | Schultz | 260/429 R |
| 3,705,919 | 12/1972 | Heck | 260/429 R |

OTHER PUBLICATIONS

Heck, J.A.C.S., 90:20, pp. 5542–5545 (1968).

*Primary Examiner*—Helen M. S. Sneed
*Attorney, Agent, or Firm*—Zarley, McKee, Thomte & Voorhees

[57] ABSTRACT

Pi-allyl-palladium compounds are prepared by reacting a vinylmercuric salt with an olefin and a palladium (II) salt.

18 Claims, No Drawings

METHOD OF SYNTHESIS OF PI-ALLYL-PALLADIUM COMPOUNDS

BACKGROUND OF THE INVENTION

Pi-allyl-palladium compounds have been reported in the literature and have been found useful as chemical intermediates and catalysts. Such compounds have gained increasing importance as catalysts for reactions of olefins and other unsaturated organic molecules, for example, processes of oligomerization. Additionally, such compounds have found use as catalysts in the cyclo-oligomerization of mono- and diolefins. For example, pi-allyl-palladium compounds can be used successfully as catalysts for the cyclo-oligomerization of 1,3-diolefins, particularly butadiene, to produce cyclododecatriene.

Although the pi-allyl-palladium compounds have been known to be useful catalysts in the types of reactions expressed herein, there has been some difficulty in obtaining these compounds in sufficiently high quantities to make them practically available for commercial organic synthesis operations. This is so because the pi-allyl-palladium compounds are frequently difficult to isolate from reaction mixtures and are quite often obtained in very low yields.

Moreover, in many prior processing methods of preparation of pi-allyl-palladium compounds, the general approach has been to first synthesize the entire organic structure of the desired pi-allyl-palladium compound and thereafter, as a last processing reaction step, to complex the organic structure with a palladium salt. Such methods have only met with limited success. Many of the reactions produce the desired organic structures only in limited quantities, with numerous side products, and require rather severe reaction conditions, carefully controlled to within well-defined limits. In addition, many of the prior art reactions which first involve formation of the organic moiety and thereafter complexing that moiety with the palladium, involve reactions which are not tolerant of substituted functional groups on the organic moiety.

Accordingly, it is the principal object of this invention to provide a method of synthesizing pi-allyl-palladium compounds wherein the desired pi-allyl-palladium compound is formed by reacting two organic molecules of relatively simple structure with a palladium (II) salt wherein a carbon-to-carbon bond is formed between the two organic molecules, with the resulting organic moiety complexing with the palladium to provide the desired pi-allyl-palladium complex.

In addition, it is an object of this invention to provide a reaction which can be run under mild conditions, which yields the desired pi-allyl-palladium compounds in high yields, often in excess of 80%, and in many cases, in excess of 90%.

Yet another object of this invention is to provide a reaction which will yield the pi-allyl-palladium compounds, with the reaction being tolerant to functional groups positioned on one or more of the organic reacting reagents, without adversely affecting the reaction.

Still another object of this invention is to provide a process of preparing pi-allyl-palladium compounds which meets each of the above-mentioned objectives by reacting a vinylmercuric salt and an olefin, preferably a terminal bond-containing olefin, with a palladium (II) salt.

The method of accomplishing these and other objects of the invention will become apparent from the following detailed description of the invention.

SUMMARY OF THE INVENTION

This invention relates to a method of preparing pi-allyl-palladium compounds comprising reacting a vinyl mercuric salt with an olefin and a palladium (II) halide salt to provide carbon-carbon bond formation between carbon atoms of the vinyl mercuric salt and the olefin. The vinyl mercuric salt and the olefin are pre-selected so that after carbon-carbon bond formation, and complexing with the palladium (II) salt, the desired pi-allyl-palladium compound is obtained.

DETAILED DESCRIPTION OF THE INVENTION.

Pi-allyl-palladium complexes are characterized by a complex formation between a paladium moiety and an allylic moiety of an organic ligand, as illustrated by the following formula:

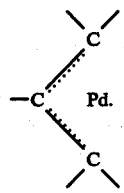

wherein the dotted line designation represents a delocalized electron system between the three indicated carbon atoms, which delocalized system is considered to at least partially donate electrons to the palladium moiety, thereby forming the pi-allyl complex. The palladium is additionally bonded to another moiety; e.g., an anion such as chloride or bromide, and the complex is considered to exist in the form of a dimer. In terms of the class of pi-allyl palladium chloride complexes, the simplest member is pi-allyl palladium chloride which is represented by the formula:

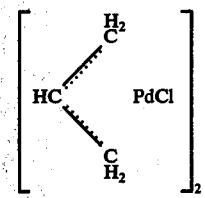

and is given the systematic name of di-$\mu$-chloro-di-pi-allyl dipalladium. Such dimers have all of the carbon and hydrogen moieties of the compound existing in a single plane, with the palladium atom sitting above the plane of the rest of the compound, along with the halogen atom. That is to say, each pi-allyl-palladium chloride molecule, for example, is associated with a second molecule sandwiched on top of it to form a dimer. In accord with the process of this invention, the pi-allyl-palladium compounds are prepared by reacting a vinyl mercuric salt with an olefin and a palladium (II) salt. The vinyl mercuric salt may be represented by the following formula:

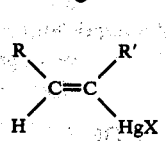

Vinyl mercurials are readily available through acetylene addition reactions. See, for example:

R. C. Larock and H. C. Brown, *J. Organometal Chem.*, 36, 1 (1972)

R. C. Larock, S. K. Gupta, and H. C. Brown, *J. Amer. Chem. Soc.*, 94, 4371 (1972).

H. Staub, K. P. Zeller, and H. Leditschke, in Houben-Weyl's "Methoden der Organischen Chemie," 4th Ed., Vol. 13, G. Thieme Verlag, Stuttgart, 1974, Pt. 2b, pp 192-199.

The above are incorporated herein by reference.

With regard to the formula presented herein for the vinyl mercuric salt, X represents the anion of that salt and may be any of the common frequently employed anions but is preferably a halide. For example, X may be a nitrate, an acetate, a sulfate, a phosphate, a chloride, a bromide, an iodide, or the like. As will be explained in more detail below, preferably X is a halide, and preferably is the same anion as the anion of the palladium (II) salt employed in the reaction.

No criticality exists with regard to the R and R' moieties. They are, of course, selected to represent such moieties on the preselected pi-allyl-palladium complex which is being synthesized. For example, R and R' may be the same or different monovalent organic hydrocarbon radicals and may be aliphatic, alicyclic, or aromatic radicals. R and R' may be hydrogen, alkyl, aralkyl, aryl and straight or branched chain. Preferably, R and R' are lower, up to $C_{12}$, straight or branched chain alkyls, and lower straight or branched chain aralkyls. For example, R and R' may be hydrogen, methyl, ethyl, propyl, butyl, phenyl, benzyl, tertiary butyl, or the like. In addition, R and R' may contain functionally substituted reactive sites since the reaction presented herein is tolerant to such functional groups as carboxyl, keto, cyano groups or other like reactive groups. Finally, the hydrogen moiety in the previously presented generic equation for the vinylmercuric salt may be replaced by groups such as those previously discussed herein for R and R'.

In summary, R and R', and if desired, the hydrogen moiety as well, of the vinylmercuric salt may be nearly any organic radical. The precise radical employed is not critical. However, certain preferred radicals are conveniently employed as previously specified herein. The exact structure of the moiety selected for R and R' is dependent upon the preselected pi-allyl-palladium complex which is to be synthesized.

The vinylmercuric salt is reacted with an olefin of the following general formula:

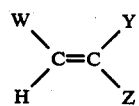

Again, there is no precise criticality for the moieties, W, Y and Z. They may be the same or different but in general are organic radicals and may be aliphatic, alicyclic, or aromatic radicals, such as alkyl, aryl, aralkyl, or the like. Preferably, they are lower ($C_{12}$ and below) radicals and they may be functionally substituted if so desired. In addition, they may be a cyano group, an ester group, a ketone group, or the like. It is, however, preferred that W be hydrogen and that the olefin has a terminal double bond. It has been found that much higher yields of product are obtained when W is hydrogen, or in other words, the olefin employed in reaction has a terminal double bond. Of course, the olefin does have at least one vinyl hydrogen atom. In other words, the olefin reactant must have at least one hydrogen atom bonded to a carbon atom of the unsaturated double bond. Of course, where W is also hydrogen the olefin is the preferred form of the invention having a terminal double bond. Such compounds are well known and can be, for example, many of the straight and branched chain aliphatic olefins including hydrocarbons such as propene, butene, isobutene, pentene, hexene and many others such as those shown in the examples below.

The palladium (II) salts employed in forming the pi-allyl-palladium complexes according to the synthesis of this invention are palladium (II) salts of any of the conventional anions. They include the halides, such as chloride, bromide and iodide, the sulfates, the nitrates, the acetates, the phosphates, the propionates, and others known to those skilled in the art. In summary, the precise anion of the palladium salt employed is not critical.

It is, however, preferred that the reaction be conducted in the presence of an alkali metal salt, as well as the palladium salt. The employment of an alkali metal salt in addition to the palladium salts helps in dissolving the palladium salt. Best results are obtained when the alkali metal salt is a metal halide salt such as a chloride or bromide as illustrated by sodium chloride, potassium bromide, lithium chloride, lithium bromide, and the like. Most preferably the palladium (II) salt is a palladium halide salt and a reaction equivalent amount of the salt is employed with the addition of a lithium halide salt as well. The most preferred salt is palladium chloride, and it is preferred that the reaction is conducted in the presence of lithium chloride. In this instance, the reaction ingredient is often referred to as lithium palladium chloride having the formula: $Li_2PdCl_4$ The added metal salt when one is employed may be added to the reaction mixture separately or alternatively added jointly with the palladium salt in the form of a coordination complex such as lithium palladium chloride.

As heretofore briefly mentioned, it is preferred that the vinylmercuric salt be a halide salt and it is also preferred that the palladium (II) salt be a halide salt, with both salts being the same halide anion. This is so simply in order to prevent the pi-allyl-palladium complex synthesized by the process of this invention from having a mixture of halide anion moieties in the resulting pi-allyl-palladium compound.

The reaction may be conducted in the presence of an organic solvent or without an organic solvent. However, where the reaction is conducted without the use of a solvent, it is preferred that the vinylmercuric salt be at least partially soluble in the olefin and most preferably is wholly soluble in the olefin employed in the reaction. Where a solvent is employed, the solvent must be a polar reaction solvent which is inert to the reaction ingredients. Suitable solvents which may be employed are tetrahydrofuran, methyl alcohol, diethyl ether, hexamethylphosphoramide, acetonitrile and the like. It is also preferred that the reaction be conducted in the presence of an excess of the olefin reaction ingredient. By "excess" it is meant that the amount of the olefin reaction ingredient employed is in excess of the stoichiometric amount. Since two reaction equivalents is a stoichiometric amount, it is preferred that more than two reaction equivalents be employed, and up to as many as ten reaction equivalents be employed. The employment of greater than stoichiometric amounts of the olefin reaction ingredient seems to assure the production of the desired pi-allyl-palladium compound in high yield.

While the description of this application has been given with particular reference to the production of pi-allyl-palladium compounds, it should also be understood that the process may be equally applicable to the production of other pi-allyl-metal complex salts such as the corresponding rhodium compounds, the corresponding ruthenium compounds, and the corresponding platinum compounds.

As heretofore mentioned, relatively mild reaction conditions may be employed. Reaction temperatures are not critical and the reaction may be conducted at temperatures of from 0° C. up to room temperature or even higher with satisfactory results. The reaction may be conducted most typically at atmospheric pressure but if desired, other pressure conditions may be employed although little advantage is gained. In addition, the reaction may be conducted under inert gases to provide a wholly inert environment for the reaction. Time is also not a critical factor for the reaction of this invention and the reaction may be conducted within a variety of time limits. In most cases, the reaction is completed within fifteen minutes to one hour, although if desired, overnight reaction times may be employed.

Sterically, the pi-allyl-palladium compound, which is in fact a dimer, as previously discussed, may be represented as follows:

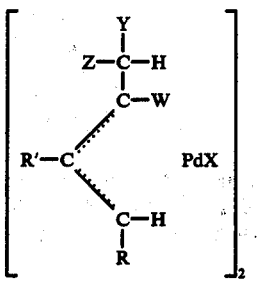

As heretofore mentioned, the palladium and the chloride moiety exist in a different plane than the remaining organic portion of the molecule and can be thought of as rising in a vertical plane from the flat horizontal plane of the remaining portion of the molecule. The precise organic radicals represented by W, Y and Z will depend upon the olefin employed and the values for R and R' will depend upon the vinylmercuric salt which is employed.

Having now described the reaction of the invention in general terms, the following specific examples are offered to illustrate but not limit the process of the invention.

EXAMPLE 1-12

Preparation of Pi-allyl-palladium compounds.

The following procedure for the preparation of di μ-chloro di (6-carboethoxy-2,2-dimethylhex-3-enyl) dipalladium (II) (Example 10) is representative. Anhydrous lithium chloride (20 mmol) and palladium chloride (10 mmol) were added to a well-dried round bottom flask previously flushed with nitrogen and containing a septum inlet and a nitrogen inlet tube. One hundred ml dry tetrahydrofuran (THF) was added via syringe to the flask and the flask cooled to 0° C. Ethyl acrylate (100 mmol) was added via syringe to the flask. Trans-tert-butylethenylmercuric chloride (10 mmol) was then added to the flask while backflushing with nitrogen. The well-stirred reaction mixture was then allowed to slowly warm to room temperature and stirred overnight. Diethyl ether and activated carbon were added to the reaction mixture which was filtered and washed with saturated aqueous ammonium chloride. The combined aqueous washings were reextracted with ether. The combined ether extractions were then dried over anhydrous sodium sulfate. Removal of the solvent provided 2.82g (87%) of reasonably pure pi-allyl palladium compound.

All other compounds shown in the table were prepared in a similar fashion with only minor modifications in the workup portion of the procedure for two of the products. In the reaction of trans-tert-butylethenylmercuric chloride and acrylonitrile (example 1), it was necessary to add THF to help solubilize the product in the ethereal solution before the ammonium chloride work-up. In the reaction of styrylmercuric chloride and ethyl acrylate (example 11), it was necessary to completely replace the ether by THF in order to solubilize the product throughout the work-up.

Recrystallization of the Pi-allyl palladium compounds occasionally proved difficult. No general solvent could be found. Disregarding the differences in solvents used, three methods of purification were used. If the product solution stripped down to an oily solid or oil the solution was triturated with pentane. The pentane solution was then cooled to precipitate the product. If the product was obtained as a solid it was recrystallized by either of two methods. If thermally stable the product was recrystallized in the normal manner by warming in an appropriate solvent, filtering, cooling and collecting the crystals. Otherwise the product was dissolved at room temperature in the appropriate solvent and filtered. The solution was then stripped down until product just began to precipitate, as evidenced by a cloudy solution, and cooled to afford recrystallized product.

In the table below, R and R' refer to the previously discussed moieties of the vinyl mercuric salt, and W, Y and Z refer to previously discussed moieties of the olefin reactant. The resulting Pi-allyl-palladium compound has the general formula presented above with the values of R, R', W, Y and Z as presented in the table.

| Example | R | R' | W | Y | Z | Crude Yield % | Recryst. Yield % |
|---|---|---|---|---|---|---|---|
| 1 | tert-C₄H₉ | H | H | H | CN | 87 | 71 |
| 2 | tert-C₄H₉ | H | H | H | H | 92 | — |
| 3 | tert-C₄H₉ | H | H | H | n-C₄H₉ | 67 | 63 |

-continued

| Example | R | R' | W | Y | Z | Crude Yield % | Recryst. Yield % |
|---|---|---|---|---|---|---|---|
| 4 | tert-C$_4$H$_9$ | H | H | H | $-\underset{\underset{O}{\|\|}}{C}CH_3$ | 103 | 67 |
| 5 | tert-C$_4$H$_9$ | H | H | CH$_3$ | $-\underset{\underset{O}{\|\|}}{C}-OCH_3$ | 29 | 22 |
| 6 | tert-C$_4$H$_9$ | H | H | CH$_3$ | CH$_3$ | 41 | 21 |
| 7 | tert-C$_4$H$_9$ | H | CH$_3$ | CH$_3$ | CH$_3$ | 19 | Not completed |
| 8 | tert-C$_4$H$_9$ | H | CH$_3$ | CH$_3$ | H | 51 | 37 |
| 9 | n-C$_4$H$_9$ | H | H | H | $-\underset{\underset{O}{\|\|}}{C}OCH_2CH_3$ | 66 | |
| 10 | tert-C$_4$H$_9$ | H | H | H | $-\underset{\underset{O}{\|\|}}{C}OCH_2CH_3$ | 87 | |
| 11 | C$_6$H$_5$ | H | H | H | $-\underset{\underset{O}{\|\|}}{C}OCH_2CH_3$ | 102 | 58 |
| 12 | tert-C$_4$H$_9$ | CH$_3$ | H | H | $-\underset{\underset{O}{\|\|}}{C}OCH_2CH_3$ | 97 | 60 |

What is claimed is:

1. A method of preparing pi-allyl-palladium compounds, said method comprising:
reacting a vinylmercuric salt the anion of said salt being selected from the group consisting of nitrate, acetate, sulfate, phosphate, and halide, with an olefin of the formula:

$$\underset{H}{\overset{W}{\diagdown}}C=C\underset{Z}{\overset{Y}{\diagup}}$$

wherein W, Y and Z are selected from the group consisting of aliphatic, alicyclic and aromatic organic radicals, and a palladium (II) salt to provide carbon-carbon bond formation between carbon atoms of said vinylmercuric salt and said olefin.

2. The method of claim 1 wherein said vinylmercuric salt is a vinylmercuric halide.

3. The method of claim 2 wherein said palladium (II) salt is a palladium halide salt.

4. The method of claim 3 wherein said vinylmercuric halide and said palladium (II) halide salt both have the same halide anion.

5. The method of claim 3 wherein said reaction is conducted in the presence of a soluble alkali metal salt.

6. The method of claim 5 wherein said soluble alkali metal salt is lithium chloride.

7. The method of claim 1 wherein said vinylmercuric salt is at least partially soluble in said olefin.

8. The method of claim 1 wherein said reaction is conducted in the presence of a polar reaction solvent which is inert to the reaction ingredients.

9. The method of claim 1 wherein said reaction is conducted in the presence of in excess of the stoichiometric amount of said olefin.

10. A method of preparing a preselected pi-allyl palladium compound, said method comprising:
reacting a vinylmercuric halide salt with an olefin of the formula:

$$\underset{H}{\overset{W}{\diagdown}}C=C\underset{Z}{\overset{Y}{\diagup}}$$

wherein W, Y and Z are selected from the group consisting of aliphatic, alicyclic and aromatic organic radicals and a palladium (II) halide salt to provide carbon-carbon bond formation between carbon atoms of said vinylmercuric halide salt and said olefin, said vinylmercuric halide salt and said olefin being preselected so that after said carbon-carbon bond formation, and complexing with said palladium salt, said preselected pi-allyl-palladium compound is obtained.

11. The method of claim 10 wherein said vinylmercuric halide salt and said palladium (II) halide salt both have the same halide anion.

12. The method of claim 11 wherein said reaction is conducted in the presence of in excess of the stoichiometric amount of said olefin.

13. A method of preparing pi-allyl-palladium compounds, said method comprising:
reacting a vinylmercuric halide salt of the formula:

$$\underset{H}{\overset{R}{\diagdown}}C=C\underset{HgX}{\overset{R'}{\diagup}}$$

wherein R and R' are organic radicals selected from the group consisting of hydrogen, alkyl, aryl, aralkyl and X is a halide anion, with an olefin of the formula:

$$\underset{H}{\overset{W}{\diagdown}}C=C\underset{Z}{\overset{Y}{\diagup}}$$

wherein, W, Y and Z are monovalent organic radicals selected from the group consisting of hydrogen, alkyl, aryl, aralkyl, and with a palladium (II) halide salt, to provide carbon-carbon bond formation between carbon atoms of said vinylmercuric halide salt and said olefin, R, R', W, Y and Z being preselected to represent organic moieties of said pi-allyl-palladium halide.

14. The method of claim 13 wherein W is hydrogen.

15. The method of claim 14 wherein X and the halide of said palladium (II) halide salt are the same halide.

16. The method of claim 14 wherein X is chloride.

17. The method of claim 16 wherein said reaction is conducted in the presence of in excess of the stoichiometric amount of said olefin.

18. The method of claim 17 wherein said reaction is conducted in the presence of an inert polar solvent.

* * * * *